(12) United States Patent
Reevell (10) Patent No.: US 12,350,423 B2
(45) Date of Patent: Jul. 8, 2025

(54) AEROSOL-GENERATING SYSTEM COMPRISING MULTIPLE AEROSOL-FORMING SUBSTRATES AND A TRANSFER ELEMENT

(71) Applicant: Altria Client Services LLC, Richmond, VA (US)

(72) Inventor: Tony Reevell, London (GB)

(73) Assignee: ALTRIA CLIENT SERVICES LLC, Richmond, VA (US)

(*) Notice: Subject to any disclaimer, the term of this patent is extended or adjusted under 35 U.S.C. 154(b) by 551 days.

(21) Appl. No.: 17/032,722

(22) Filed: Sep. 25, 2020

(65) Prior Publication Data
US 2021/0007398 A1    Jan. 14, 2021

Related U.S. Application Data

(63) Continuation of application No. 15/844,809, filed on Dec. 18, 2017, now Pat. No. 10,820,633, which is a
(Continued)

(30) Foreign Application Priority Data

Dec. 19, 2016 (EP) ..................... 16205101

(51) Int. Cl.
*A24F 40/30* (2020.01)
*A24F 40/40* (2020.01)
(Continued)

(52) U.S. Cl.
CPC ........... *A61M 11/042* (2014.02); *A24F 40/30* (2020.01); *A24F 40/40* (2020.01); *A24F 40/42* (2020.01);
(Continued)

(58) Field of Classification Search
CPC ...... H05B 3/10–18; A24F 40/00; A24F 40/10; A24F 40/20; A24F 40/30;
(Continued)

(56) References Cited

U.S. PATENT DOCUMENTS

| 4,854,331 A | 8/1989 | Banerjee et al. |
| 5,067,499 A | 11/1991 | Banerjee et al. |

(Continued)

FOREIGN PATENT DOCUMENTS

| CN | 10268867 | 9/2008 |
| CN | 201878765 U | 6/2011 |

(Continued)

OTHER PUBLICATIONS

Chinese Office Action and English translation thereof dated Jul. 30, 2021.
(Continued)

*Primary Examiner* — Tiffany T Tran
(74) *Attorney, Agent, or Firm* — Harness, Dickey & Pierce, P.L.C.

(57) ABSTRACT

A cartridge and an aerosol-generating device. The cartridge includes a cartridge housing, a first aerosol-forming substrate in the cartridge housing and a second aerosol-forming substrate in the cartridge housing. An aerosol-generating device defines a cavity configured to receive at least a portion of the cartridge along a first direction and the aerosol-generating device includes a transfer element extending from an end wall of the cavity, the transfer element having a longitudinal axis extending substantially parallel to the first direction, the transfer element contacts the second aerosol-forming substrate when the portion of the cartridge is in the cavity, an electric heater including a resistive heating coil wrapped around a portion of the transfer element, the resistive heating coil being wrapped
(Continued)

around the longitudinal axis of the transfer element, a power supply, and a controller configured to control a supply of electrical power from the power supply to the electric heater.

12 Claims, 3 Drawing Sheets

Related U.S. Application Data continuation of application No. PCT/EP2017/081409, filed on Dec. 4, 2017.

(51) Int. Cl.
| | | |
|---|---|---|
| *A24F 40/42* | (2020.01) | |
| *A24F 40/44* | (2020.01) | |
| *A61M 11/04* | (2006.01) | |
| *A61M 15/06* | (2006.01) | |
| *A24F 40/10* | (2020.01) | |
| *A24F 40/20* | (2020.01) | |
| *A61M 16/10* | (2006.01) | |

(52) U.S. Cl.
CPC .............. *A24F 40/44* (2020.01); *A61M 15/06* (2013.01); *A24F 40/10* (2020.01); *A24F 40/20* (2020.01); *A61M 16/107* (2014.02); *A61M 2205/8206* (2013.01)

(58) Field of Classification Search
CPC .... A24F 40/40–42; A24F 40/50; A24F 40/44; A61M 11/041–042; A61M 15/06; A61M 16/107; A61M 2205/8206
See application file for complete search history.

(56) References Cited

U.S. PATENT DOCUMENTS

| | | | |
|---|---|---|---|
| 2006/0130857 A1* | 6/2006 | Roth ..................... A24F 42/60 | 131/273 |
| 2007/0023056 A1 | 2/2007 | Cantrell et al. | |
| 2008/0092912 A1 | 4/2008 | Robinson et al. | |
| 2013/0014772 A1 | 1/2013 | Liu | |
| 2013/0037041 A1* | 2/2013 | Worm ..................... A24F 40/46 | 131/329 |
| 2013/0333700 A1 | 12/2013 | Buchberger | |
| 2014/0166029 A1 | 6/2014 | Weigensberg et al. | |
| 2014/0305449 A1* | 10/2014 | Plojoux ................... A24F 40/46 | 131/328 |
| 2015/0040929 A1* | 2/2015 | Hon ........................ A24F 40/42 | 392/394 |
| 2016/0000147 A1* | 1/2016 | Li .......................... A24F 40/485 | 392/404 |
| 2016/0073695 A1 | 3/2016 | Sears et al. | |
| 2016/0081395 A1* | 3/2016 | Thorens ................ A61M 11/042 | 392/390 |
| 2016/0286862 A1* | 10/2016 | Silvetrini ............... A24F 40/485 | |
| 2016/0324216 A1 | 11/2016 | Li et al. | |
| 2016/0345631 A1 | 12/2016 | Monsees et al. | |
| 2017/0258138 A1 | 9/2017 | Rostami et al. | |
| 2018/0020723 A1* | 1/2018 | Davis ................... A61M 11/042 | 392/404 |
| 2018/0297048 A1* | 10/2018 | Ricketts ............... B65D 51/285 | |
| 2018/0325174 A1* | 11/2018 | Sutton ....................... A24B 9/00 | |
| 2019/0124982 A1 | 5/2019 | Atkins et al. | |
| 2019/0357590 A1 | 11/2019 | Sutton | |

FOREIGN PATENT DOCUMENTS

| | | | | |
|---|---|---|---|---|
| CN | 203828070 U | | 9/2014 | |
| CN | 104970444 A | | 10/2015 | |
| CN | 105072936 A | * | 11/2015 | ............. A24F 42/20 |
| CN | 106068084 A | | 11/2016 | |
| CN | 106102490 A | | 11/2016 | |
| EP | 2282649 A1 | | 2/2011 | |
| EP | 2460424 A1 | * | 6/2012 | ............. A24F 40/40 |
| EP | 3009017 A1 | | 4/2016 | |
| EP | 3061359 A1 | | 8/2016 | |
| JP | 2013-545473 A | | 12/2013 | |
| RU | 2600092 C2 | | 10/2016 | |
| TW | 201206357 A | | 2/2012 | |
| WO | WO-2014/110119 A1 | | 7/2014 | |
| WO | WO-2015/0179388 A1 | | 11/2015 | |
| WO | WO-2015/197627 A1 | | 12/2015 | |
| WO | WO-2016005602 A1 | * | 1/2016 | ........... A24B 15/167 |
| WO | WO-2016/079152 A1 | | 5/2016 | |
| WO | WO-2016079151 A1 | * | 5/2016 | ............. A24F 40/43 |
| WO | WO-2016159013 A1 | * | 10/2016 | ............. A24F 40/48 |

OTHER PUBLICATIONS

Chinese Notice of Allowance and Search Report mailed Mar. 28, 2022.
Russian Decision to Grant and Search Report and English translation thereof dated Mar. 15, 2021.
Japanese Office Action and English translation thereof dated Dec. 15, 2021.
Extended European Search Report for European Application No. 16205101.5 Dated Jul. 12, 2017.
www.reuters.com/article/us-brit-am-tobacco-products-idUSKCN0T71U020151118 <https://protect-us.mimecast.com/s/Jq6bBvC9X01ho> last accessed Dec. 18, 2017.
http://jinjiatech.com/PRODUCTS/Heat/91 <https://protect-us.mimecast.com/s/X8vqBguOLaRfM> last accessed Dec. 18, 2017.
International Search Report and Written Opinion dated Jan. 8, 2018.
International Preliminary Report on Patentability dated Jul. 4, 2019.
Japanese Decision to Grant and English translation thereof dated Mar. 28, 2022.
Korean Notice of Allowance Corresponding to Application No. 10-2019-7015642, dated Feb. 3, 2023.

* cited by examiner

AEROSOL-GENERATING SYSTEM COMPRISING MULTIPLE AEROSOL-FORMING SUBSTRATES AND A TRANSFER ELEMENT

CROSS-REFERENCE TO RELATED APPLICATIONS

This application is a continuation of, and claims priority under 35 U.S.C. § 120 to, U.S. application Ser. No. 15/844,809, filed Dec. 18, 2017, which is a continuation of International Application No. PCT/EP2017/081409, filed on Dec. 4, 2017, and further claims priority under 35 U.S.C. § 119 to European Patent Application No. 16205101.5, filed on Dec. 19, 2016, the entire contents of each of which are herein incorporated by reference.

BACKGROUND

At least some example embodiments relate to an aerosol-generating system such as an electrically operated smoking system. The aerosol-generating system comprises a cartridge having first and second aerosol-forming substrates, and an aerosol-generating device having a transfer element.

One type of aerosol-generating system is an electrically operated smoking system. Handheld electrically operated smoking systems typically comprise an aerosol-generating device comprising a battery, control electronics and an electric heater for heating an aerosol-forming substrate. The aerosol-forming substrate may be contained within part of the aerosol-generating device. For example, the aerosol-generating device may comprise a liquid storage portion in which a liquid aerosol-forming substrate, such as a nicotine solution, is stored. Such devices, often referred to as electronic vapor (e-vapor) devices, typically contain sufficient liquid aerosol-forming substrate to provide a number of uses equivalent to consuming multiple conventional cigarettes.

In an attempt to provide adult vapers with an experience that more closely simulates the experience of consuming a cigarette, some devices have attempted to combine an e-vapor configuration with a tobacco-based substrate to impart a tobacco taste to the aerosol inhaled by the adult vaper.

SUMMARY

Such devices may be impractically large and require the adult vaper to change a tobacco component and a liquid component at different times.

It would be desirable to provide an aerosol-generating system that mitigates or eliminates at least some of these problems.

According to at least one example embodiment there is provided an aerosol-generating system comprising a cartridge and an aerosol-generating device. The cartridge comprises a cartridge housing, a first aerosol-forming substrate positioned within the cartridge housing and a second aerosol-forming substrate positioned within the cartridge housing. The aerosol-generating device comprises a cavity for receiving at least a portion of the cartridge, wherein the cavity is configured for insertion of the cartridge into the cavity along a first direction. The aerosol-generating device further comprises a transfer element extending from an end wall of the cavity, the transfer element having a longitudinal axis extending substantially parallel to the first direction, wherein the aerosol-generating system is configured so that a portion of the transfer element contacts the second aerosol-forming substrate when the cartridge is in the cavity. The aerosol-generating device also comprises an electric heater comprising a resistive heating coil wrapped around a portion of the transfer element, wherein the resistive heating coil is wrapped around the longitudinal axis of the transfer element. The aerosol-generating device further comprises a power supply and a controller for controlling a supply of electrical power from the power supply to the electric heater.

At least one example embodiment provides an aerosol-generating system including a cartridge including a cartridge housing, a first aerosol-forming substrate in the cartridge housing and a second aerosol-forming substrate positioned within the cartridge housing and an aerosol-generating device defining a cavity configured to receive at least a portion of the cartridge along a first direction, the aerosol-generating device including, a transfer element extending from an end wall of the cavity, the transfer element having a longitudinal axis extending substantially parallel to the first direction, a portion of the transfer element contacts the second aerosol-forming substrate when the portion of the cartridge is in the cavity, an electric heater including a resistive heating coil wrapped around a portion of the transfer element, the resistive heating coil being wrapped around the longitudinal axis of the transfer element, a power supply, and a controller configured to control a supply of electrical power from the power supply to the electric heater.

In at least one example embodiment, the cartridge further comprises a porous carrier material, and the second aerosol-forming substrate is on the porous carrier material.

In at least one example embodiment, the transfer element contacts the porous carrier material.

In at least one example embodiment, the cartridge comprises a removable seal overlying the porous carrier material at a first end of the cartridge housing.

In at least one example embodiment, the cartridge comprises a frangible seal, and the transfer element is configured to pierce the frangible seal when the aerosol-generating device receives the cartridge.

In at least one example embodiment, the transfer element comprises a first end connected to the end wall of the cavity and a second end opposite the first end, and the second end of the transfer element defines a piercing portion configured to pierce the frangible seal.

In at least one example embodiment, a diameter of the piercing portion decreases in a direction along the longitudinal axis and towards the second end.

In at least one example embodiment, the porous carrier material has an annular shape defining a passage within the porous carrier material, and the transfer element is at least partially received within the passage when the aerosol-generating device receives the cartridge.

In at least one example embodiment, the cartridge comprises an airflow channel between the porous carrier material and the cartridge housing, and a downstream end of the airflow channel is in fluid communication with the solid aerosol-forming substrate.

In at least one example embodiment, the solid aerosol-forming substrate comprises tobacco.

In at least one example embodiment, the second aerosol-forming substrate comprises nicotine.

In at least one example embodiment, the second aerosol-forming substrate is substantially free from nicotine.

In at least one example embodiment, the first aerosol-forming substrate is solid and the second aerosol-forming substrate is liquid.

BRIEF DESCRIPTION OF THE DRAWINGS

Example embodiments are further described, by way of example only, with reference to the accompanying drawings in which.

DETAILED DESCRIPTION

Example embodiments will become more readily understood by reference to the following detailed description of the accompanying drawings. Example embodiments may, however, be embodied in many different forms and should not be construed as being limited to the example embodiments set forth herein. Rather, these example embodiments are provided so that this disclosure will be thorough and complete. Like reference numerals refer to like elements throughout the specification.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that when an element or layer is referred to as being "on", "connected to" or "coupled to" another element or layer, it can be directly on, connected or coupled to the other element or layer or intervening elements or layers may be present. In contrast, when an element is referred to as being "directly on", "directly connected to" or "directly coupled to" another element or layer, there are no intervening elements or layers present. As used herein, the term "and/or" includes any and all combinations of one or more of the associated listed items.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings set forth herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Example embodiments are described herein with reference to cross-section illustrations that are schematic illustrations of idealized embodiments (and intermediate structures). As such, variations from the shapes of the illustrations as a result, for example, of manufacturing techniques and/or tolerances, are to be expected. Thus, these example embodiments should not be construed as limited to the particular shapes of regions illustrated herein, but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of this disclosure.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and this specification and will not be interpreted in an idealized or overly formal sense unless expressly so defined herein.

Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

As used herein, the term "aerosol-forming substrate" is used to describe a substrate capable of releasing volatile compounds, which can form an aerosol. The aerosols generated from aerosol-forming substrates of aerosol-generating systems according to example embodiments may be visible or invisible and may include vapours (for example, fine particles of substances, which are in a gaseous state, that are ordinarily liquid or solid at room temperature) as well as gases and liquid droplets of condensed vapours.

Aerosol-generating systems according to example embodiments facilitate simultaneous replacement of a solid aerosol-forming substrate and a pre-aerosol formulation (e.g., a liquid aerosol-forming substrate) (also referred to as a pre-vapor formulation) by providing both substrates in a single cartridge. Advantageously, this may simplify use of the aerosol-generating system for an adult vaper when compared to known devices in which a tobacco-based substrate and a nicotine solution must be replaced or replenished separately.

Providing a solid aerosol-forming substrate and a liquid aerosol-forming substrate in a single cartridge may simplify replenishment of the liquid aerosol-forming substrate when compared to known devices in which an adult vaper may be required to refill a reservoir forming part of the device itself. Simplifying replenishment of the liquid aerosol-forming substrate may advantageously facilitate a reduction in the amount of liquid aerosol-forming substrate provided in the cartridge when compared to the amount of liquid aerosol-forming substrate provided in known devices. Advantageously, this may allow aerosol-generating systems according to example embodiments to be smaller than known devices.

Aerosol-generating systems according to example embodiments provide a heater section that is separate from the cartridge. Advantageously, this may reduce the cost and simplify the manufacture of the cartridge when compared to known devices in which a heater and a liquid aerosol-forming substrate are combined into a single part of an aerosol-generating device. Advantageously, providing a heater section that is separate from the cartridge may facilitate cleaning of the electric heater, which may facilitate use of the heater section with multiple cartridges.

Advantageously, a transfer element (e.g., a liquid transfer element) may facilitate contact between the liquid aerosol-forming substrate and the electric heater during use of the aerosol-generating system. That is, the liquid transfer element facilitates transfer of the liquid aerosol-forming substrate from the cartridge to the electric heater, for example by capillary action.

The liquid transfer element may comprise any suitable material or combination of materials which is able to convey the liquid aerosol-forming substrate along its length. The liquid transfer element may be formed from a porous material, but this need not be the case. The liquid transfer element may be formed from a material having a fibrous or spongy structure. In an example embodiment, the liquid transfer element comprises a bundle of capillaries. For example, the liquid transfer element may comprise a plurality of fibres or threads or other fine bore tubes. The liquid transfer element may comprise sponge-like or foam-like material. The structure of the liquid transfer element may form a plurality of small bores or tubes, through which the liquid aerosol-forming substrate can be transported by capillary action. The particular material or materials will depend on the physical properties of the liquid aerosol-forming substrate. Examples of suitable capillary materials include a sponge or foam material, ceramic- or graphite-based materials in the form of fibres or sintered powders, foamed metal or plastics material, a fibrous material, for example made of spun or extruded fibres, such as cellulose acetate, polyester, or bonded polyolefin, polyethylene, terylene or polypropylene fibres, nylon fibres, ceramic, glass fibres, silica glass fibres, carbon fibres, metallic fibres of medical grade stainless steel alloys such as austenitic 316 stainless steel and martensitic 440 and 420 stainless steels. The liquid transfer element may have any suitable capillarity so as to be used with different liquid physical properties. The liquid aerosol-forming substrate has physical properties, including but not limited to viscosity, surface tension, density, thermal conductivity, boiling point and vapour pressure, which allow the liquid aerosol-forming substrate to be transported through the liquid transfer element. The liquid transfer element may be formed from heat-resistant material. The liquid transfer element may comprise a plurality of fibre strands. The plurality of fibre strands may be generally aligned along a length of the liquid transfer element.

In an example embodiment, the aerosol-generating system comprises at least one airflow inlet and at least one airflow outlet. During use, air flows through the aerosol-generating system along a flow path from the airflow inlet to the airflow outlet. Air flows along the flow path from an upstream end of the flow path at the airflow inlet to a downstream end of the flow path at the airflow outlet. The aerosol-generating system may be configured so that, in use, the solid aerosol-generating substrate is positioned downstream of the liquid aerosol-generating substrate.

The cartridge may comprise a porous carrier material, wherein the liquid aerosol-forming substrate is provided on the porous carrier material. Advantageously, providing the liquid aerosol-forming substrate on a porous carrier material may reduce the risk of the liquid aerosol-forming substrate leaking from the cartridge.

The porous carrier material and the liquid transfer element may comprise the same material. Alternatively, the porous carrier material and the liquid transfer element comprise different materials.

The porous carrier material may comprise any suitable material or combination of materials which is permeable to the liquid aerosol-forming substrate and allows the liquid aerosol-forming substrate to migrate through the porous carrier material. In an example embodiment, the material or combination of materials is inert with respect to the liquid aerosol-forming substrate. The porous carrier material may or may not be a capillary material. The porous carrier material may comprise a hydrophilic material to improve distribution and spread of the liquid aerosol-forming substrate. This may assist with consistent aerosol formation. The particular material or materials will depend on the physical properties of the liquid aerosol-forming substrate. Examples of suitable materials are a capillary material, for example a sponge or foam material, ceramic- or graphite-based materials in the form of fibres or sintered powders, a foamed metal or plastics material, a fibrous material, for example made of spun or extruded fibres, such as cellulose acetate, polyester, or bonded polyolefin, polyethylene, terylene or polypropylene fibres, nylon fibres or ceramic. The porous carrier material may have any suitable porosity so as to be used with different liquid physical properties.

In an example embodiment, the aerosol-generating system is configured so that, in use, the liquid transfer element contacts the porous carrier material.

The cartridge may comprise a removable seal overlying the porous carrier material at a first end of the cartridge housing. In an example embodiment, the first end is the upstream end of the cartridge housing. The removable seal may be secured to the cartridge housing about a periphery of the removable seal. The removable seal may be secured to the cartridge housing by at least one of an adhesive and a weld, such as an ultrasonic weld. The removable seal may be formed from a sheet material. The sheet material may comprise at least one of a polymeric film and a metallic foil. The removable seal may be configured for removal from the cartridge by adult vaper before combining the cartridge with the aerosol-generating device. The removable seal may comprise a pull tab to facilitate removal of the seal.

The cartridge may comprise a frangible seal. Advantageously, a frangible seal may prevent the loss of volatile compounds from one or both of the solid aerosol-forming substrate and the liquid aerosol-forming substrate. The frangible seal may extend across an opening defined by the cartridge housing. The frangible seal may extend across an end of the cartridge housing. In an example embodiment, the frangible seal extends across an upstream end of the cartridge housing. The frangible seal may be secured to the cartridge housing about a periphery of the frangible seal. The frangible seal may be secured to the cartridge housing by at least one of an adhesive and a weld, such as an ultrasonic weld. The frangible seal may be formed from a sheet material. The sheet material may comprise at least one of a polymeric film and a metallic foil.

In an example embodiment, the liquid transfer element is configured to pierce the frangible seal when the aerosol-generating device receives the cartridge. Advantageously, the liquid transfer element may automatically pierce the frangible seal when the aerosol-generating device and the heater section are combined with the cartridge.

The liquid transfer element may comprise a first end connected to the end wall of the cavity and a second end opposite the first end. In an example embodiment, the second end of the liquid transfer element defines a piercing portion configured to pierce the frangible seal when the aerosol-generating device receives the cartridge. The diameter of the piercing portion may decrease in a direction along the longitudinal axis and towards the second end. That is, the second end of the liquid transfer element may comprise a tapered portion. Advantageously, this may reduce the force required for the liquid transfer element to pierce the frangible seal. The second end of the liquid transfer element tapers to a point.

The porous carrier material may have an annular shape defining a passage through the porous carrier material. The passage may be a through-passage extending completely through the porous carrier material. The passage may be a blind-passage having an open end and a closed end. In an example embodiment, the open end is positioned at the upstream end of the porous carrier material.

In an example embodiment, the aerosol-generating system is configured so that the liquid transfer element is at least partially received within the passage when the aerosol-generating device receives the cartridge. Advantageously, this may maximise the contact area between the liquid transfer element and the porous carrier material.

In an example embodiment, the cartridge comprises an airflow channel positioned between the porous carrier material and the cartridge housing. In an example embodiment, an airflow inlet of the aerosol-generating system is in fluid communication with an upstream end of the airflow channel. The electric heater is in fluid communication with both the airflow inlet and the upstream end of the airflow channel. In an example embodiment, a downstream end of the airflow channel is in fluid communication with the solid aerosol-forming substrate. The downstream end of the airflow channel is in fluid communication with an upstream end of the solid aerosol-forming substrate. A downstream end of the solid aerosol-forming substrate is in fluid communication with an airflow outlet of the aerosol-generating system.

In an example embodiment, the resistive heating coil is wound around a first end of the liquid transfer element. In embodiments in which the cartridge comprises a porous carrier material, the aerosol-generating system is configured so that the resistive heating coil does not contact the porous carrier material when the cartridge is received within the cavity. In embodiments in which the porous carrier material has an annular shape and comprises a passage extending through the porous carrier material, the resistive heating coil is wound around a first end of the liquid transfer element. Only a second end of the liquid transfer element is received within the passage when the cartridge is received within the cavity.

The pitch of the resistive heating coil is may be between about 0.5 millimetres and about 1.5 millimetres, such as about 1.5 millimetres. The pitch of the resistive heating coil means the spacing between adjacent turns of the coil. The coil may comprise fewer than six turns, and may have fewer than five turns. The coil may be formed from an electrically resistive wire having a diameter of between about 0.10 millimetres and about 0.15 millimetres, such as about 0.125 millimetres. The electrically resistive wire may be formed of 904 or 301 stainless steel. Examples of other suitable metals include titanium, zirconium, tantalum and metals from the platinum group. Examples of other suitable metal alloys include, Constantan, nickel-, cobalt-, chromium-, aluminium-titanium-zirconium-, hafnium-, niobium-, molybdenum-, tantalum-, tungsten-, tin-, gallium-, manganese- and iron-containing alloys, and super-alloys based on nickel, iron, cobalt, stainless steel, Timetal®, iron-aluminium based alloys and iron-manganese-aluminium based alloys. The resistive heating coil may also comprise a metal foil, such as an aluminium foil, which is provided in the form of a ribbon.

The cartridge housing is may be tubular and comprises a first, upstream end and a second, downstream end. In an example embodiment, the solid aerosol-forming substrate is positioned within the downstream end. The porous carrier material is positioned within the upstream end.

The porous carrier material may be positioned directly within the cartridge housing. In an example embodiment, the porous carrier material is retained within the cartridge housing by an interference fit.

The porous carrier material may be positioned within a liquid storage housing, wherein the liquid storage housing is positioned within the cartridge housing. The liquid storage housing may be retained within the cartridge housing by an interference fit.

In embodiments in which the cartridge comprises an airflow channel positioned between the porous carrier material and the cartridge housing, an outer surface of the liquid storage housing may be shaped to define the airflow channel between the cartridge housing and the liquid storage housing when the liquid storage housing is received within the cartridge housing. The outer surface of the liquid storage housing may comprise a groove to define the airflow channel when the liquid storage housing is received within the cartridge housing.

The liquid storage housing may be tubular. In embodiments in which the cartridge comprises a removable seal or a frangible seal, the seal may extend across the upstream end of the liquid storage housing. In an example embodiment, the seal is secured to the liquid storage housing instead of the cartridge housing.

The tubular liquid storage housing may have an open upstream end and a closed downstream end. In embodiments in which the cartridge comprises a removable seal or a frangible seal, the seal may extend across the upstream end of the liquid storage housing so that the porous carrier material is positioned between the seal and the closed end.

The solid aerosol-forming substrate may be retained in the cartridge housing by an interference fit.

The cartridge may comprise a filter positioned downstream of the solid aerosol-forming substrate. The filter may comprise a plug of filter material positioned within the downstream end of the cartridge housing. The plug of filter material may be retained within the cartridge housing by an interference fit. The filter may comprise a sheet material extending across a downstream opening of the cartridge housing. The sheet material may comprise a mesh. The sheet material may be secured to the cartridge housing by at least one of an adhesive and a weld, such as an ultrasonic weld. The filter may retain the solid aerosol-forming substrate in the cartridge housing.

The aerosol-generating system may comprise a mouthpiece. In embodiments in which the aerosol-generating system comprises at least one airflow outlet, the mouthpiece may comprise the at least one airflow outlet. The mouthpiece may form part of the cartridge. The mouthpiece may form part of the aerosol-generating device. The mouthpiece may be formed separately from the cartridge and the aerosol-generating device, wherein at least one of the cartridge and the aerosol-generating device is configured to receive the mouthpiece.

The solid aerosol-forming substrate may comprise tobacco. The solid aerosol-forming substrate may comprise a tobacco-containing material containing volatile tobacco flavour compounds which are released from the substrate upon heating.

The solid aerosol-forming substrate may comprise tobacco containing deprotonated nicotine. Deprotonating the nicotine within tobacco may advantageously increase the volatility of the nicotine. Nicotine may be deprotonated by subjecting the tobacco to an alkalising treatment.

The solid aerosol-forming substrate may comprise a non-tobacco material. The solid aerosol-forming substrate may comprise tobacco-containing material and non-tobacco containing material.

The solid aerosol-forming substrate may include at least one aerosol-former. As used herein, the term 'aerosol former' is used to describe any suitable known compound or mixture of compounds that, in use, facilitates formation of an aerosol. Suitable aerosol-formers include, but are not limited to: polyhydric alcohols, such as propylene glycol, triethylene glycol, 1,3-butanediol and glycerine; esters of polyhydric alcohols, such as glycerol mono-, di- or triacetate; and aliphatic esters of mono-, di- or polycarboxylic acids, such as dimethyl dodecanedioate and dimethyl tetradecanedioate In an example embodiment, aerosol formers are polyhydric alcohols or mixtures thereof, such as propylene glycol, triethylene glycol, 1,3-butanediol and glycerine.

The solid aerosol-forming substrate may comprise a single aerosol former. Alternatively, the solid aerosol-forming substrate may comprise a combination of two or more aerosol formers.

The solid aerosol-forming substrate may have an aerosol former content of greater than 5 percent on a dry weight basis.

The solid aerosol-forming substrate may have an aerosol former content of between approximately 5 percent and approximately 30 percent on a dry weight basis.

The solid aerosol-forming substrate may have an aerosol former content of approximately 20 percent on a dry weight basis.

The liquid aerosol-forming substrate may comprise a tobacco-containing material comprising volatile tobacco flavour compounds which are released from the liquid upon heating. The liquid aerosol-forming substrate may comprise a non-tobacco material. The liquid aerosol-forming substrate may include water, solvents, ethanol, plant extracts and natural or artificial flavours. The liquid aerosol-forming substrate comprises an aerosol former. Suitable aerosol formers include polyhydric alcohols or mixtures thereof, such as propylene glycol, triethylene glycol, 1,3-butanediol and glycerine.

The liquid aerosol-forming substrate may comprise nicotine.

The liquid aerosol-forming substrate may be free from nicotine. In such embodiments, the vaporised liquid aerosol-forming substrate may be drawn through the solid aerosol-forming substrate during use to strip one or more volatile compounds from the solid aerosol-forming substrate. The vaporised liquid aerosol-forming substrate may strip nicotine from the solid-aerosol-forming substrate. A solid aerosol-forming substrate comprising tobacco containing deprotonated nicotine may be particularly suited to embodiments in which the liquid aerosol-forming substrate is free from nicotine.

The power supply may comprise a battery. For example, the power supply may be a nickel-metal hydride battery, a nickel cadmium battery, or a lithium based battery, for example a lithium-cobalt, a lithium-iron-phosphate or a lithium-polymer battery. The power supply may alternatively be another form of charge storage device such as a capacitor. The power supply may require recharging and may have a capacity that allows for the storage of enough energy for use of the aerosol-generating device with more than one cartridge.

Figure 1:
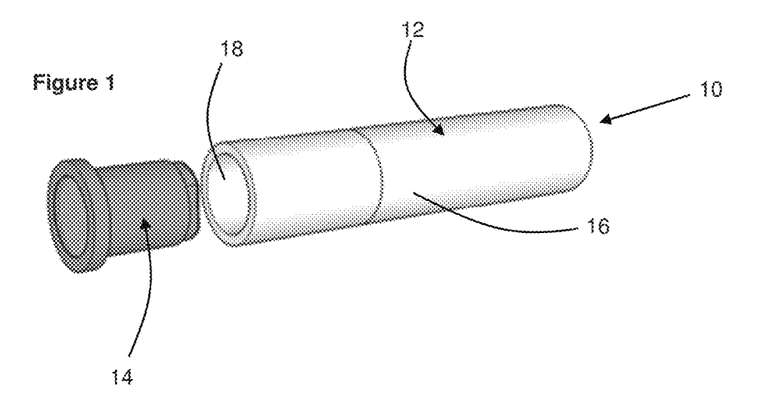
FIG. 1 shows a perspective view of an aerosol-generating system according to an example embodiment with a cartridge separate from an aerosol-generating device.
Figure 2:
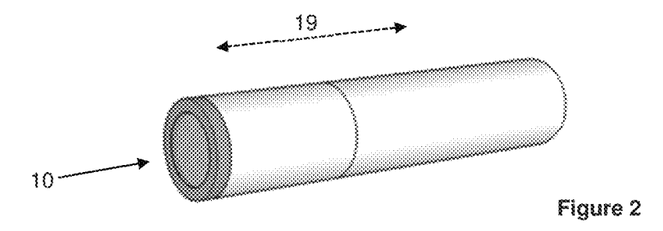
FIG. 2 shows a perspective view of the aerosol-generating system of FIG. 1 with the cartridge inserted into the aerosol-generating device.

FIGS. 1 and 2 show an aerosol-generating system 10 according to an example embodiment. The aerosol-generating system 10 comprises an aerosol-generating device 12 and a cartridge 14. The aerosol-generating device 10 comprises a device housing 16 defining a cavity 18 for receiving an upstream end of the cartridge 14. FIG. 1 shows the cartridge 14 separate from the aerosol-generating device 12 and FIG. 2 shows the cartridge 14 received within the cavity 18 of the aerosol-generating device 12. The cavity 18 is configured for insertion of the cartridge 14 into the cavity 18 along a first direction 19.

Figure 3:
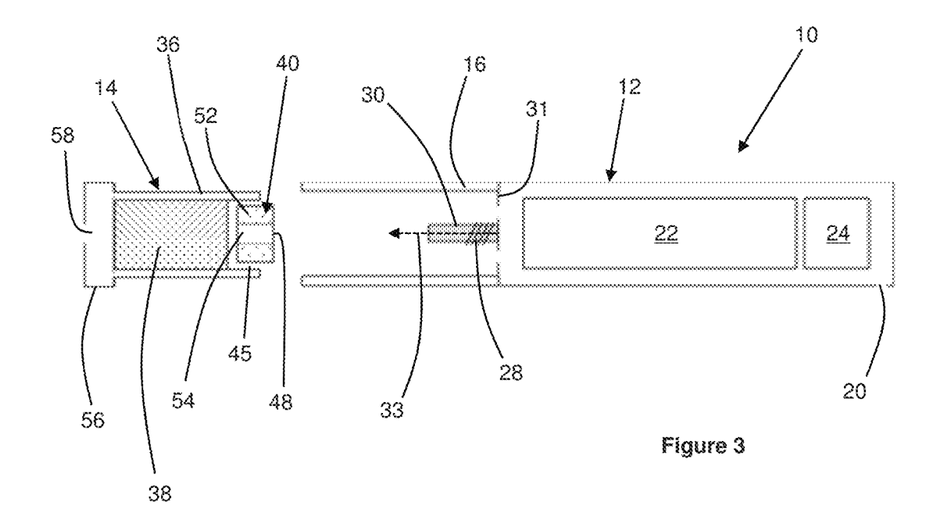
FIG. 3 shows a cross-sectional view of the aerosol-generating system of FIG. 1 with the cartridge separate from the aerosol-generating device.

FIG. 3 shows a cross-sectional view of the aerosol-generating system 10. The aerosol-generating device 12 comprises an airflow inlet 20 positioned at an upstream end of the device housing 16. A power supply 22 and a controller 24 are positioned within the upstream end of the device housing 16. While not illustrated, the controller 24 and the power supply 22 are connected such that the power supply 22 provides power to the controller 24.

The aerosol-generating system 10 further comprises an electric heater 28 comprising a resistive heating coil, and a liquid transfer element 30 extending from an end wall 31 of the cavity 18. The resistive heating coil is wound around a first, upstream end of the liquid transfer element 30. The liquid transfer element 30 has a longitudinal axis 33 that extends substantially parallel to the first direction 19, and the resistive heating coil is wound around the longitudinal axis 33. During use, the controller 24 controls a supply of electrical power from the power supply 22 to the electric heater 28.

Figure 5:
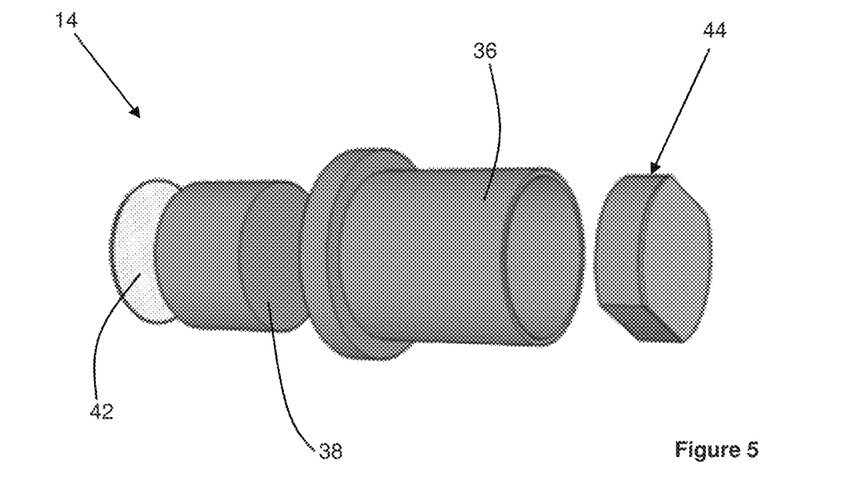
FIG. 5 shows an exploded view of the cartridge of the aerosol-generating system of FIG. 1.

The cartridge 14 comprises a cartridge housing 36, and a solid aerosol-forming substrate 38 and a liquid aerosol-forming substrate 40 both positioned within the cartridge housing 36. FIG. 5 shows an exploded view of the cartridge 14.

The solid aerosol-forming substrate 38 comprises a tobacco plug positioned within the downstream end of the cartridge housing 36. A mesh filter 42 is attached to a downstream end of the cartridge housing 36 to retain the tobacco plug within the cartridge housing 36.

The liquid aerosol-forming substrate 40 is contained within a liquid storage assembly 44 positioned within the upstream end of the cartridge housing 36. The liquid storage assembly 44 is shown in more detail in a further exploded view in FIG. 6.

Figure 6:
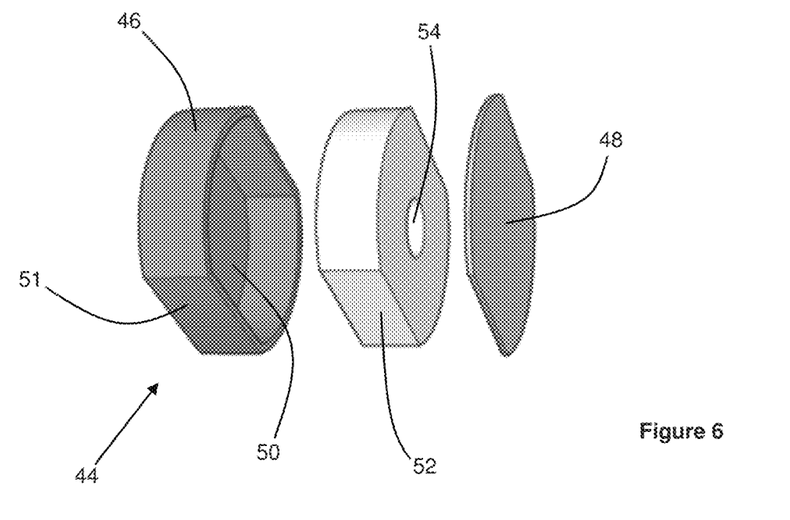
FIG. 6 shows an exploded view of a portion of the cartridge of FIG. 5 to show the porous carrier material and the liquid aerosol-forming substrate.

The liquid storage assembly 44 comprises a tubular liquid storage housing 46 that is retained within the upstream end of the cartridge housing 36 by an interference fit. A frangible seal 48 extends across and is secured to the upstream end of the tubular liquid storage housing 46. The tubular liquid storage housing 46 has a closed downstream end 50 and a porous carrier material 52 is positioned within the tubular liquid storage housing 46 between the frangible seal 48 and the closed downstream end 50 of the tubular liquid storage housing 46. The liquid aerosol-forming substrate 40 is absorbed into the porous carrier material 52. The porous carrier material 52 has an annular shape and defines a passage 54 through the porous carrier material 52, the passage 54 extending between the frangible seal 48 and the closed downstream end 50 of the tubular liquid storage housing 46. When the liquid storage assembly 44 is received within the cartridge housing 36, planar side walls 51 of the tubular cartridge housing 46 are spaced apart from the cartridge housing 36 to create airflow passages 45 between the liquid storage assembly 44 and the cartridge housing 36.

The downstream end of the cartridge housing 36 forms a mouthpiece 56, the mouthpiece 56 defining an airflow outlet 58 of the aerosol-generating system 10.

Figure 4:
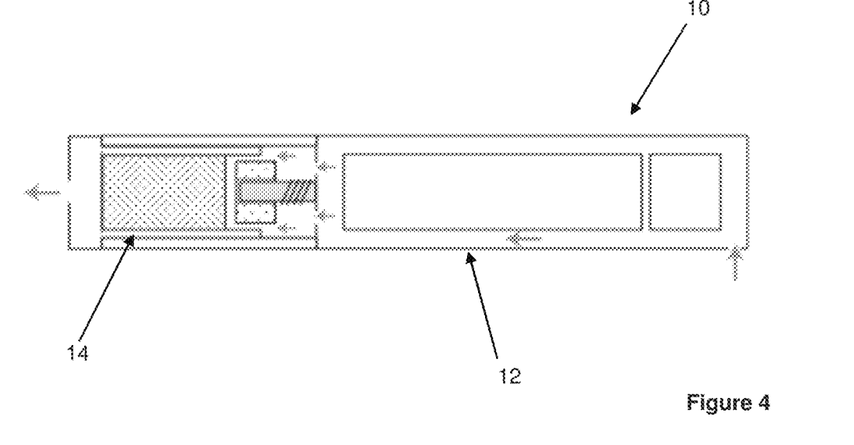
FIG. 4 shows a cross-sectional view of the aerosol-generating system of FIG. 1 with the cartridge inserted into the aerosol-generating device.

FIG. 4 shows a cross-sectional view of the aerosol-generating system 10 after the cartridge 14 has been inserted into the cavity 18 of the aerosol-generating device 12. When the cartridge 14 is inserted into the cavity 18 a second, downstream end of the liquid transfer element pierces the frangible seal 48 of the liquid storage assembly 44. Liquid aerosol-forming substrate 40 is wicked along the liquid transfer element 30 to the electric heater 28 where it is vaporised. When an adult vaper applies a negative pressure on the mouthpiece 56, air is drawn into the aerosol-generating system 10 through the airflow inlet 20, through the aerosol-generating device 12, across the electric heater 28 where liquid aerosol-forming substrate vapour is entrained in the airflow, through the airflow passages 45 and through the solid aerosol-forming substrate 38 where further volatile compounds are entrained in the airflow, and out through the airflow outlet 58. The controller 24 supplies energy to the electric heater 28 such that the electric heater 28 can vaporize the liquid aerosol-forming substrate.

The invention claimed is:

1. An aerosol-generating system comprising:
   a cartridge including a cartridge housing, the cartridge housing including a first aerosol-forming substrate, the first aerosol-forming substrate being a solid aerosol-forming substrate in a downstream end of the cartridge housing, and
   a liquid storage assembly in an upstream end of the cartridge housing, the liquid storage assembly including a liquid storage housing with a closed downstream end, a porous carrier material including a second aerosol-forming substrate and a passage, and a frangible seal, the second aerosol-forming substrate being a liquid aerosol-forming substrate, the porous carrier material being entirely disposed between the closed downstream end of the liquid storage housing and the frangible seal, and the passage extending through the porous carrier material from the closed downstream end of the liquid storage housing to the frangible seal; and
   an aerosol-generating device defining a cavity configured to receive at least a portion of the cartridge along a first direction, the aerosol-generating device including,
   a transfer element extending from an end wall of the cavity, the transfer element having a longitudinal axis extending substantially parallel to the first direction, the transfer element including a first end connected to the end wall of the cavity and a second end opposite the first end, and the second end of the transfer element being tapered to a point to define a piercing portion configured to pierce the frangible seal of the cartridge and extend through the passage to the closed downstream end, without piercing the closed downstream end, of the liquid storage housing when the aerosol-generating device receives the cartridge,
   an electric heater including a resistive heating coil wrapped around a portion of the transfer element, the resistive heating coil being wrapped around the longitudinal axis of the transfer element,
   a power supply, and
   a controller configured to control a supply of electrical power from the power supply to the electric heater.

2. The aerosol-generating system according to claim 1, wherein the second aerosol-forming substrate is on the porous carrier material.

3. The aerosol-generating system according to claim 1, wherein the transfer element contacts the porous carrier material.

4. The aerosol-generating system according to claim 1, wherein the frangible seal is a removable seal overlying the porous carrier material at the upstream end of the cartridge housing.

5. The aerosol-generating system according to claim 1, wherein the transfer element is configured to pierce the frangible seal when the aerosol-generating device receives the cartridge.

6. The aerosol-generating system according to claim 1, wherein a diameter of the piercing portion decreases in a direction along the longitudinal axis and towards the second end.

7. The aerosol-generating system according to claim 1, wherein the porous carrier material has an annular shape defining the passage within the porous carrier material, and the transfer element is at least partially received within the passage when the aerosol-generating device receives the cartridge.

8. The aerosol-generating system according to claim 1, wherein the cartridge comprises an airflow channel between planar side walls of the liquid storage housing and the cartridge housing, and a downstream end of the airflow channel is in fluid communication with the first aerosol-forming substrate.

9. The aerosol-generating system according to claim 8, wherein the airflow channel is free from the first aerosol-forming substrate and the second aerosol-forming substrate.

10. The aerosol-generating system according to claim 1, wherein the first aerosol-forming substrate comprises tobacco.

11. The aerosol-generating system according to claim 1, wherein the second aerosol-forming substrate comprises nicotine.

12. The aerosol-generating system according to claim 1, wherein the second aerosol-forming substrate is substantially free from nicotine.

* * * * *

UNITED STATES PATENT AND TRADEMARK OFFICE
CERTIFICATE OF CORRECTION

| | |
|---|---|
| PATENT NO. | : 12,350,423 B2 |
| APPLICATION NO. | : 17/032722 |
| DATED | : July 8, 2025 |
| INVENTOR(S) | : Tony Reevell |

Page 1 of 1

It is certified that error appears in the above-identified patent and that said Letters Patent is hereby corrected as shown below:

On the Title Page (*) Notice Should read:
-- Subject to any disclaimer, the term of this patent is extended or adjusted under 35 U.S.C. 154(b) by 551 days.
This patent is subject to a terminal disclaimer. --

Signed and Sealed this
Twenty-seventh Day of January, 2026

John A. Squires
*Director of the United States Patent and Trademark Office*